United States Patent [19]

Buxton et al.

[11] Patent Number: 4,754,597
[45] Date of Patent: Jul. 5, 1988

[54] SOLID SHAPED ARTICLES

[75] Inventors: Ian R. Buxton, High Wycombe; Harold Feldman, Liphook, both of England

[73] Assignee: John Wyeth & Brother Ltd., Maidenhead, England

[21] Appl. No.: 31,225

[22] Filed: Mar. 30, 1987

Related U.S. Application Data

[63] Continuation of Ser. No. 445,138, Nov. 26, 1982, abandoned.

[30] Foreign Application Priority Data

Dec. 11, 1981 [GB] United Kingdom ............... 8137525

[51] Int. Cl.⁴ ............................................. B65B 63/00
[52] U.S. Cl. ............................................ 53/440; 34/5; 53/431; 53/432
[58] Field of Search ............... 53/440, 431, 432; 34/5; 264/28

[56] References Cited

U.S. PATENT DOCUMENTS

| | | | |
|---|---|---|---|
| 3,269,905 | 8/1966 | Damaskus et al. | 167/58 |
| 3,579,360 | 5/1971 | Rey et al. | 34/5 X |
| 3,669,663 | 6/1972 | Wheelock | 264/28 X |
| 3,855,712 | 12/1974 | Blonde | 34/5 |
| 3,925,903 | 12/1975 | Ward | 34/5 X |
| 4,021,280 | 5/1977 | Rinde et al. | 264/28 X |
| 4,305,502 | 12/1981 | Gregory et al. | 206/532 |
| 4,371,516 | 2/1983 | Gregory et al. | 424/22 |

FOREIGN PATENT DOCUMENTS

| | | | |
|---|---|---|---|
| 0019929 | 5/1980 | European Pat. Off. | |
| 0084705 | 1/1987 | European Pat. Off. | |
| 1382158 | 11/1964 | France | |
| 801856 | 9/1958 | United Kingdom | 34/5 |
| 1061557 | 3/1967 | United Kingdom | |

OTHER PUBLICATIONS

Hackh's Chemical Dictionary, McGraw Hill, pp. 7, 153, 249.

*Primary Examiner*—Robert L. Spruill
*Assistant Examiner*—Steven P. Weihrouch
*Attorney, Agent, or Firm*—Arthur E. Wilfond; Richard A. Elder; Ronald W. Alice

[57] ABSTRACT

Solid shaped articles, particularly rapidly dissolving pharmaceutical dosage forms, carrying predetermined unit quantities of chemicals are prepared by a novel process involving the addition of the predetermined amount of chemical in a solvent to a placebo article which contains a network of carrier material. The placebo article is prepared by freezing a composition of carrier material in a solvent and subliming the solvent from the frozen composition.

6 Claims, No Drawings

SOLID SHAPED ARTICLES

This application is a continuation, of application Ser. No. 445,138, filed Nov. 26, 1982, now abandoned.

This invention relates to a solid shaped article carrying a predetermined unit quantity of a chemical and more particularly to a novel process for preparing such an article.

It is known to produce shaped articles carrying chemicals by a process involving sublimation of a solvent from a composition in the solid state comprising the chemical and a solution in a solvent of a carrier material. U.S. Pat. Nos. 4,305,502 and 4,371,516 claim priority from the same U.K. applications as French Pat. No. 2,366,835, and which issued as U.K. Pat. No. 1,548,022. These patents disclose such a method of preparing solid shaped articles which are rapidly disintegrated by water and in which a network of carrier material carries a predetermined amount of a chemical, particularly a pharmaceutical substance. Such rapidly disintegratable solid shaped articles are useful for many different applications, particularly where it is desired to administer, dispense or otherwise utilise a chemical in predetermined unit quantities. For example, certain chemicals which are used in solution or suspension form but which are difficult or hazardous to transport or store in such form may be converted into a solid form which can be added by the user to an aqueous medium to produce the desired solution or dispersion containing a predetermined amount of the chemical. Further, the chemical may be a chemical reagent such that the product may be added to a known amount of aqueous liquid to produce a standardised liquid composition which can be used, for example, in chemical analysis. Further, the chemical may be a diagnostic compound which it is desired to add to a biological sample (e.g. blood, urine) in order to determine the amount of a particular constituent present in the sample. However preferably the chemical is a pharmaceutical substance and the solid shaped article carrying the predetermined unit quantity of pharmaceutical substance is a pharmaceutical dosage form.

These pharmaceutical dosage forms are particularly suitable for oral administration. When orally administered the pharmaceutical dosage forms generally disintegrate rapidly in the mouth (e.g. within one or two seconds) and thus the dosage form is a particularly advantageous means for administering pharmaceuticals to humans, and also to non-human animals. Such dosage forms can be used as alternatives to tablets, pills or capsules, particularly to patients who have difficulty in swallowing conventional dosage forms.

The aforementioned specifications describe a process for preparing the shaped articles in which a composition comprising the predetermined amount of chemical and a solution in a solvent (such as water) of a water-soluble or water-dispersible carrier material is frozen in a mould and the solvent is then sublimed from the frozen composition so as to produce a network of the carrier material carrying the chemical. We have now found an alternative process of preparing shaped articles which process has advantages over the known process.

According to the present invention there is provided a process for preparing a solid shaped article carrying a predetermined unit quantity of a chemical, which process comprises freezing a composition comprising a solution in a first solvent of a water-soluble or water-dispersible carrier material that is inert towards the chemical, subliming the first solvent from the frozen composition so as to produce a product having a network of carrier material, adding to said product a solution or suspension of a second non-aqueous solvent containing the predetermined amount of the chemical and allowing or causing the second solvent to evaporate.

According to one embodiment of the process, the composition is frozen in a mould corresponding to the size and shape of the desired shaped article and the first solvent is sublimed, for example in a freeze drier, while the frozen composition is still in the mould. The predetermined amount of chemical may then be dosed on to the resulting sublimed product while it is in the mould or alternatively the sublimed product may be removed from the mould before the chemical is dosed on to it. In this embodiment the mould can be, for example a depression in a metal plate (e.g. an aluminium plate). The plate may contain more than one depression, each depression being of the size and shape corresponding to the desired size of the shaped article. However the mould is preferably a depression in a sheet of filmic material. The filmic material may contain more than one depression. The filmic material may be similar to that employed in conventional blister packs which are used for packaging oral contraceptive tablets and like medicament forms. For example the filmic material may be made of thermoplastic material with the depressions formed by thermoforming. The preferred filmic material is a polyvinyl chloride film. Laminates of filmic material such as polyvinyl chloride/polyvinylidene chloride, polyvinyl chloride/polytetrafluorethylene or polyvinyl chloride/polyvinylidene chloride/polyethylene may also be used. If the chemical is dosed on to the sublimed products while the latter are still in depressions in a sheet of filmic material a covering sheet may be adhered to the filmic material so as to produce a package enclosing the shaped articles. The covering sheet is preferably an aluminium foil or aluminium foil laminate which may be adhered to the filmic material around the depressions by, for example, a heat sensitive adhesive. The covering sheet is preferably adhered to the filmic material such that it may be peeled away from the filmic material by the user so as to expose the dosage forms in their depressions.

In an alternative embodiment of the process of the invention, the frozen and sublimed product prior to dosing with the chemical may be of a size corresponding to the desired size of two or more shaped articles. For example the composition may be frozen in a tray and the solvent sublimed from the frozen composition to produce a slab or a sheet of sublimed product corresponding in size to that of a number of the desired shaped articles. The sheet may be subdivided to form products of the desired size and the chemical in the second solvent dosed on to the subdivided products. The subdivision of the sheet does not need to be carried out accurately since the measured amount of the chemical is added to the subdivided products. If the second solvent does not diffuse excessively through the sheet of sublimed product, the sheet may be dosed with the predetermined amount of chemical at selected positions on the sheet prior to subdivision and the sheet subsequently subdivided to give shaped articles each containing the predetermined amount of chemical.

The carrier material is preferably chosen so that the shaped article (e.g. a pharmaceutical dosage form when the chemical is a pharmaceutical substance) is rapidly disintegrated by water. Preferably the carrier is chosen so that the product disintegrates in water within 5 seconds at 20° C.

The disintegration time of the product can be determined to see whether it is capable of being disintegrated by water at 20° C. within 5 seconds using a standard tablet disintegration apparatus as described in British Pharmacopoeia, 1980, Vol II, Appendix XII A but with the standard 2.00 mm wire mesh replaced by stainless steel 40 mesh screen. A sample product is placed in a dry tube held above the surface of the water. The apparatus is started and the sample immersed in water at 20° C. The sample should disperse on the liquid surface and any solid residue should pass through the 40 mesh screen within 5 seconds.

Examples of suitable carrier materials, particularly those that are pharmaceutically acceptable for use in preparing pharmaceutical dosage forms, are described in the above mentioned U.K. and French patent specifications. For example, the carrier may be formed from polypeptides such as gelatin, particularly gelatin which is partially hydrolysed, e.g. by heating in water. For example, the gelatin may be partially hydrolysed by heating a solution of the gelatin in water, e.g. in an autoclave at about 120° C. for up to 2 hours, e.g. from about 5 minutes to about 1 hour, preferably from about 30 minutes to about 1 hour. The hydrolysed gelatin is preferably used at concentrations of about 1% to 6% weight/vol., most preferably at 2% to 4% e.g. about 3%. Other carrier materials may be used in place of partially hydrolysed gelatin for example polysaccharides such as dextran. (In particular dextran of average molecular weight from 60,000 to 75,000 e.g. 150,000 to 200,000). The dextran is preferably used at concentration of about 10% weight/volume e.g. about 6% to 8% (if mol weight is 150,000 to 200,000) or about 6% (if mol weight is up to 275,000).

Water is preferably employed, as the solvent in the composition which is frozen and sublimed. An additional co-solvent (such as an alcohol) may also be used if it is desired to improve the solubility, dispersability or wettability of any of the ingredients of the composition. The composition may contain ingredients additional to the carrier material. For example the composition may include fillers (e.g. mannitol, sorbitol) which improve the physical properties of the shaped articles when preparing pharmaceutical dosage forms. The dosage form may include pharmaceutically acceptable adjuvants such as colouring agents, flavouring agents, preservatives and the like. Such adjuvants may be included in the composition to be frozen and sublimed or alternatively may be added subsequently, e.g. with the pharmaceutical substance or other chemical in the second solvent.

The composition may be frozen and the solvent sublimed by the general procedure described in the above mentioned patent specifications. For example the composition may be frozen by the use of solid carbon dioxide or liquid nitrogen. In a preferred method of freezing, the composition is passed through a freezing tunnel into which liquid nitrogen is injected, the liquid nitrogen being vapourised and the resulting cold gaseous nitrogen being passed over the composition.

When the composition has been frozen the solvent is sublimed from it. If desired, the frozen compositions may be stored in a cold store before the sublimation process is carried out. The sublimation may be carried out in a freeze drier by subjecting the frozen composition in the mould to reduced pressure and, if desired, controlled application of heat to aid the sublimation. The pressure can be below about 4 mm Hg, e.g. below 0.3 mm Hg, for example 0.1 to 0.2 mm or even below 0.05 mm Hg. The initial temperature in the freeze drier may be, for example, as high as 60° C. and this temperature can be reduced (e.g. to 40° C.) as the temperature of the frozen composition increases.

The predetermined amount of chemical is dosed on to the sublimed product in the second solvent. Preferably a solution of the chemical is used. The second solvent has to be non-aqueous and be compatible with the chemical so as to form a solution, or less preferably a readily dispersible suspension. The second solvent should also be compatible with the carrier material. It is not necessary that the carrier material is completely inert in the second solvent provided that the solvent does not adversely effect the desired properties of the shaped article. Preferably the solvent is volatile so that the evaporation of the solvent after dosing takes place rapidly. The evaporation can take place, by, for example, maintaining the shaped articles at room temperature or higher temperatures (e.g. 35° to 40° C.). When preparing pharmaceutical dosage forms it is preferable that the solvent should be pharmaceutically acceptable although this is not essential since the solvent is removed in the evaporation step.

When the carrier material is hydrolysed gelatin suitable second solvents include, for example, chloroform, dichloromethane, trichloroethylene and isopropanol and mixtures thereof. When the carrier material is dextran suitable solvents include acetone, ethanol, chloroform, diethyl ether, dichloroethane and isopropanol and mixtures thereof. The choice of solvent will depend on the chemical to be dispensed, not all chemicals being soluble in all the solvents. When the chemical is a benzodiazepine (e.g. lormetazepam, oxazepam, lorazepam, temazepam) preferred solvents are chloroform, dichloromethane and trichloroethylene (hydrolysed gelatin carrier) or acetone, chloroform and dichloroethane (dextran carrier). Many other pharmaceutical substances including those disclosed in the above mentioned specifications can be dosed in a similar manner. The process of the invention is particularly suited to pharmaceutical substances used in low dose such as the benzodiazepines, cyclopenthiazide and oral contraceptive steroids as well as especially moisture intolerant drugs such as digoxin.

The second solvent containing the chemical may be dispensed on to the products of the sublimation stage, by, for example, means of a micropipette. The concentration of the chemical in the solvent is adjusted so that the predetermined amount of chemical can be dispensed in a suitable volume of solvent. The volume of solvent dispensed per individual product may be, for example 0.01 to 3 ml e.g. about 0.1 ml.

The process of the invention has advantages over the process described in the above mentioned specifications. For example the process of the invention is applicable to some chemicals which cannot be employed in the process of the prior art, in particular chemicals which would react with solvent (e.g. water) used for the carrier material. In addition the process of the present invention enables large quantities of the placebo products to be prepared and stored so that different chemicals (e.g. pharmaceutical substances) can be added to smaller quantities of the placebo freeze dried product when required. This enables large scale production of the placebo products to be carried out even if only a small quantity of a particular final active product is required e.g. individual dosages of medicaments can be prepared for individual patients. In addition the process enables a slab or sheet of material to be freeze dried and then dosed and this embodiment of the invention has the extra advantages over the prior process employing individual moulds that the space in the freeze dryer is utilised more economically so enabling the unit cost of the final products to be lower.

The following examples illustrate the invention.

EXAMPLE 1

PREPARATION OF PHARMACEUTICAL DOSAGE FORMS USING HYDROLYSED GELATIN AS CARRIER MATERIAL (a) Preparation of 3% hydrolysed gelatin solution Gelatin B.P.: 30.00 g.
Purified water to: 1000.00 ml.

The gelatin is dissolved in the water with the aid of heat and constant stirring. The resulting solution is autoclaved at 121° C. for 60 minutes and allowed to cool to room temperature.

(b) Preparation of placebo dosage forms

Mannitol: 15.00 g.
3% hydrolysed gelatin solution to: 500.00 g.

The mannitol is dissolved in the gelatin solution at room temperature. Using a syringe 0.500 g. of the solution is dispensed into moulds consisting of cylindrical depressions in a sheet of polyvinyl chloride. The moulds containing the liquid are placed on a conveyor and passed through a current of cold nitrogen at about $-120°$ C. The frozen masses, still in their moulds are then freeze dried in a freeze drier. The pressure within the freeze drier is adjusted to 0.8 mm Hg. The temperature of the shelves in the freeze drier is set at 60° C. for 1 hour and then the pressure is lowered to 0.2 mm Hg. The resulting placebo dosage forms are removed from the freeze drier after 2½ hours. They comprise an open matrix containing no active ingredient (c) Application of active ingredient to the placebo dosage form Lormetazepam: 1.00 g.
Chloroform to: 100.00 ml.

The drug is dissolved in the solvent and made up to volume using volumetric glassware. The placebo dosage forms, prepared in (b) above, are removed from their moulds or left in situ during the dosing procedure. The solution is drawn up into the disposable tip of an automatic pipette and 0.1 ml of the solution is delivered on to each of the placebo units. The solvent is allowed to evaporate for 1 hour at room temperature before being stored at 37° C. for a further hour. The dosage forms are then stored at room temperature. If the dosage forms are in situ in their moulds, they are over-sealed with an impervious foil.

The resulting pharmaceutical dosage forms dissolve rapidly in water (within 5 secs. at 20° C.) and also in the mouth (within 2 seconds). Similar results are obtained by replacing the chloroform with dichloromethane and trichloroethylene.

EXAMPLE 2

PREPARATION OF PHARMACEUTICAL DOSAGE USING DEXTRAN AS CARRIER MATERIAL (a) Preparation of dextran solution Dextran Grade B (average M.W. 150,000–200,000): 30 g.
Deionised water to: 500 g.

The dextran is dissolved in the water employing moderate agitation.

(b) Preparation of placebo dosage forms

Step (b) of Example 1 is followed replacing the hydrolysed gelatin solution by the dextran solution from Example 2 step (a)

(c) Application of active ingredient to the placebo dosage forms

Step (c) of Example 1 is repeated substituting the placebo dosage forms from Example 2 step (b) for those of Example 1 step (b) and substituting dichloroethane for chloroform.

The resulting dosage forms dissolve rapidly in water (within 5 secs at 20° C.) and in the mouth (within 2 seconds). Similar results are obtained by replacing dichloroethane with acetone and chloroform.

EXAMPLES 3 AND 4

Placebo dosage forms are prepared according to the procedure described in Example 1(a) and (b). The following compositions of active ingredients are prepared:

Example 3 cyclopenthiazide: 0.250 g
isopropanol to: 100 ml

Example 4 clonidine: 0.1 g
chloroform to: 100 ml 0.1 ml of each composition is dosed on to each placebo such that the resulting pharmaceutical dosage forms each contain a dose of 0.25 mg cyclopenthiazide (Example 3) or 0.1 mg clonidine (Example 4)

EXAMPLES 5 AND 6

Placebo dosage forms are prepared according to the procedure described in Example 2(a) and (b). The following compositions of active ingredients are prepared:

Example 5

Digoxin: 0.125 g
Ethanol/chloroform (50:50 v/v) to: 100 ml

Example 6 ethinyl oestradiol: 0.030 g
levonorgestrel: 0.250 g
chloroform to: 100 ml 0.1 ml of each composition is dosed on to each placebo such that the resulting pharmaceutical dosage forms contain a dose of 0.125 mg digoxin (Example 5) or 30 μg ethinyloestradiol and 250 μg levonorgestrel (Example 6).

EXAMPLES 7 AND 8

Placebo units are prepared according to the procedure described in Example 2(a) and (b). The following compositions are prepared:

Example 7

Indole acetic acid: 1 g
Acetone to: 100 ml

Example 8

Indole butyric acid: 1 g
Diethyl ether to: 100 ml 0.1 ml of each composition is dosed on to each placebo unit. The resulting units from Example 7 each containml 0.1 ml of each composition is dosed on to each placebo unit. The resulting units from Example 7 each contain 1 mg of indole acetic acid and may be used as plant growth promoters by adding one unit to 1 liter of water. The units from Example 8 each contain 1 mg of indole butyric acid and these may be used as a rooting growth promoter for plant cuttings by adding one unit to 1 liter of water.

We claim:

1. A process for preparing a solid shaped article carrying a predetermined unit quantity of a chemical, which process comprises freezing a composition comprising a solution in a first solvent of a water-soluble or water-dispersible carrier material that is inert towards the chemical, subliming the first solvent from the frozen composition so as to produce a product having a network of carrier material, adding to said product a solution or suspension of a second non-aqueous solvent containing the predetermined amount of the chemical and allowing or causing the second non-aqueous solvent to evaporate from said solution or suspension.

2. The process of claim 1 wherein the composition is frozen in a mould corresponding to the size and shape of the desired shaped article and the first solvent is sublimed while the frozen composition is in the mould.

3. The process of claim 2 wherein the second solvent containing the chemical is added to the sublimed product while the sublimed product is in the mould.

4. The process of claim 1 wherein the composition is frozen in a mould corresponding to the size and shape of more than one shaped article and the sublimed product is sub-divided to the desired size and shape prior or subsequent to the addition of the second non-aqueous solvent containing the chemical.

5. The process of claim 1 wherein the carrier material is gelatin and the second solvent is at least one solvent selected from the group consisting of chloroform, dichloromethane, trichloroethylene and isopropanol.

6. The process of claim 1 wherein the carrier material is dextran and the second solvent is at least one solvent selected from the group consisting of acetone, ethanol, chloroform, diethyl ether, dichloroethane and isopropanol.

* * * * *